United States Patent
Kim et al.

(10) Patent No.: US 9,651,564 B2
(45) Date of Patent: May 16, 2017

(54) DEVICE AND METHOD FOR MEASURING HEMOGLOBIN

(71) Applicant: BODITECHMED. INC, Chuncheon-si (KR)

(72) Inventors: Byeong Chul Kim, Chuncheon-si (KR); Ki Tae Park, Chuncheon-si (KR); Cheol Min Kim, Namyangju-si (KR); Kwang Won Choi, Chuncheon-si (KR)

(73) Assignee: BODITECHMED, INC, Chuncheon-si, Gangwon-Do (KR)

( * ) Notice: Subject to any disclaimer, the term of this patent is extended or adjusted under 35 U.S.C. 154(b) by 105 days.

(21) Appl. No.: 14/391,339

(22) PCT Filed: Apr. 8, 2013

(86) PCT No.: PCT/KR2013/002901
§ 371 (c)(1),
(2) Date: Oct. 8, 2014

(87) PCT Pub. No.: WO2013/154308
PCT Pub. Date: Oct. 17, 2013

(65) Prior Publication Data
US 2015/0109608 A1    Apr. 23, 2015

(30) Foreign Application Priority Data
Apr. 13, 2012 (KR) .......... 10-2012-0038223

(51) Int. Cl.
| | |
|---|---|
| *G01N 33/72* | (2006.01) |
| *G01N 21/03* | (2006.01) |
| *G01N 21/59* | (2006.01) |
| *G01N 21/31* | (2006.01) |

(52) U.S. Cl.
CPC ........... *G01N 33/721* (2013.01); *G01N 21/03* (2013.01); *G01N 21/314* (2013.01); *G01N 21/59* (2013.01);
(Continued)

(58) Field of Classification Search
CPC ...... G01N 21/314; G01N 21/59; G01N 21/03; G01N 21/3151; G01N 21/31;
(Continued)

(56) References Cited

U.S. PATENT DOCUMENTS 5,064,282 A * 11/1991 Curtis ................... B01L 3/5027
356/246
5,298,978 A * 3/1994 Curtis ..................... B01L 3/021
250/577
(Continued)

FOREIGN PATENT DOCUMENTS

| JP | 2003-202287 A | 7/2003 |
|---|---|---|
| JP | 2004-166775 A | 6/2004 |

(Continued)

*Primary Examiner* — Gordon J Stock, Jr.
(74) *Attorney, Agent, or Firm* — Rabin & Berdo, P.C.

(57) ABSTRACT

The present invention relates to a system for measuring the hemoglobin concentration in whole blood, wherein the system comprises: a light-radiating unit including a light source that emits two types of incident light having different wavelengths; a diffusion unit which diffuses the incident light emitted by the light-radiating unit; a cuvette-holding unit which is formed so as to hold a cuvette including a blood sample; a detection unit which detects each absorbance of the two types of incident light having different wavelengths; a processing unit which determines the hemoglobin concentration in the blood by processing the measured absorbance result; and a control unit which regulates the two types of incident light having different wavelengths in order to repeatedly/sequentially radiate same. Although the system for measuring hemoglobin in whole blood of the (Continued)

present invention uses a small amount of whole blood, it is possible to measure the total hemoglobin concentration in an accurate and reliable manner. The system of the present invention aligns the paths of two types of incident light having different wavelengths passing through a microcuvette by using a diffuser plate so as to easily align a light source and increase the reliability of the results. Also, the system of the present invention uses two wavelengths so as to rapidly and accurately measure the total amount of hemoglobin, including oxidized and reduced hemoglobin.

19 Claims, 3 Drawing Sheets

(52) U.S. Cl.
CPC ....... *G01N 33/726* (2013.01); *G01N 21/3151* (2013.01); *G01N 2021/0321* (2013.01); *G01N 2201/062* (2013.01); *G01N 2201/0612* (2013.01); *G01N 2201/0634* (2013.01)

(58) Field of Classification Search
CPC ... G01N 2021/0321; G01N 2021/3144; G01N 2021/3148; G01N 2021/3155; G01N 2021/3181; G01N 33/721; G01N 33/49; G01N 33/726; G01N 33/72; G01N 33/723; G01N 33/725; G01N 2201/061; G01N 2201/0612; G01N 2201/062; G01N 2201/0634; G01J 3/42; G01J 3/427

See application file for complete search history.

(56) References Cited

U.S. PATENT DOCUMENTS

| | | | |
|---|---|---|---|
| 5,608,519 A * | 3/1997 | Gourley | G01N 15/10 250/461.2 |
| 6,262,798 B1 | 7/2001 | Shepherd et al. | |
| 6,831,733 B2 | 12/2004 | Pettersson et al. | |
| 2003/0123047 A1 | 7/2003 | Pettersson et al. | |
| 2004/0058311 A1* | 3/2004 | Fletcher | A61B 5/0059 435/4 |
| 2005/0036146 A1* | 2/2005 | Braig | G01N 21/03 356/436 |
| 2005/0048017 A1* | 3/2005 | Strassner | A61K 8/345 424/70.13 |
| 2007/0222973 A1* | 9/2007 | Hoshiko | G01N 21/253 356/39 |
| 2011/0263031 A1 | 10/2011 | Gomes et al. | |

FOREIGN PATENT DOCUMENTS

| | | |
|---|---|---|
| KR | 10-2002-0081763 A | 10/2002 |
| KR | 10-2004-0077865 A | 9/2004 |
| KR | 10-0963554 B1 | 6/2010 |
| WO | WO 01-53806 A1 | 7/2001 |

\* cited by examiner

Measuring zone

DEVICE AND METHOD FOR MEASURING HEMOGLOBIN

TECHNICAL FIELD

The present invention generally relates to a filed measuring the amount of hemoglobin in blood.

DESCRIPTION OF RELATED TECHNOLOGY

Hemoglobin is the iron containing oxygen transport metalloprotein in red blood cells of all vertebrates. The low hemoglobin count is referred to as anemia. The causes of anemia are various and the concentration of hemoglobin can be used for determining the types of anemia depending on their causes. For example, in the case of iron-deficiency anemia, the red blood cell related index decreases in contrast to the anemia caused by the lack of vitamin B12 and folic acid, where the red blood cell related index increases. In addition, there are many other types of anemia that are caused by many various reasons and that have a different red blood cell related index. Thus, it is important to measure the amount of hemoglobin in accurately diagnosing and typing anemia at the beginning. The amount of hemoglobin also serve as a sensitive indicator of the iron deficiency, which can be used for monitoring the efficacy of iron therapy and for diagnosing anemia due to the iron deficiency.

Various methods and devices are known to measure the concentration of hemoglobin. These methods can be divided into an invasive and non-invasive type which doesn't' require the use of blood. The former is further divided into a type measuring optical density of whole blood without hemolysis and a type that requires hemolysis. Non-invasive methods/devices are disclosed in KR Patent application No. 2002-0081763 which is related to non-invasive methods and devices for monitoring the concentration of hemoglobin and oxygen saturation. The non-invasive methods are appropriate for the cases where the continuous monitoring of the hemoglobin concentration is required, which results in high cost and thus is not applicable for a single measurement.

Further invasive methods for measuring the amount of hemoglobin are disclosed in U.S. Pat. No. 6,262,798, which relates to a spectrometric determination of the concentration of various hemoglobin species in whole blood. WO 2001/53806 discloses an apparatus and sample cuvette that comprise an absorption filter or an interference filter, which provides the correction for variations in the detector sensitivity and in the effective optical path length due to the varying level of scattering.

Although the invasive methods as described above have some advantages of analyzing whole blood without hemolysis, they have disadvantages that the results obtained are not consistent due to the nonhomogeneous nature of blood which usually contains many different components and to the light deflection caused by the nonhomogeneous nature of blood. Methods using hemolysis can produce accurate results because the concentration of hemoglobin is measured outside of the red blood cells. However, it has disadvantages that it requires a high cost device and complex reagent for the test. Furthermore, the reagents used have a short shelf-life due to their high hygroscopicity which requires an air tight container (for example a cuvette) with a desiccant for storage and the use of the contents in the container within several minutes after its exposure to the air.

Therefore, there is a need to develop a simple, rapid and cost effective method and device for measuring the concentration of hemoglobin from whole blood overcoming the problems of conventional method based on hemolysis and using whole blood.

DETAILED DESCRIPTION OF THE INVENTION

Problems to be Solved

To solve the problems as described above, the present invention is to provide an accurate and reproducible system and method to measure the concentration of total hemoglobin using whole blood.

SUMMARY OF THE INVENTION

One aspect of the present disclosure provides a system for measuring the concentration of hemoglobin in whole blood, which may comprise: a light radiating member comprising at least one light source, the light source emitting an incident light having a first wavelength between 520 and 590 nm and/or second wavelength of at least 800 nm; a diffuser distributing the incident light emitted from the light radiating member; a cuvette accommodating member configured to accommodate a cuvette for whole blood; a detector detecting a first absorbance of the incident light having the first wavelength which has passed through the whole blood and a second absorbance of the incident light having the second wavelength which has passed through the whole blood; a processer determining the amount of hemoglobin in the whole blood using the first and the second absorbance detected by the detector; and a controller regulating the incident light such that the incident light of the first wave length and the second wave length are radiated in order.

In one exemplary aspect of the present disclosure, the system may comprises a guide for the light source guiding the incident light to the diffuser the guide having an inner diameter; a guide for the incident light guiding the light incident upon the diffusion member to a measuring zone of the cuvette comprising the whole blood, the guide having an inner diameter; and a guide for the detector guiding the incident light that has passed through the measuring zone to the detector, the guide having an inner diameter. The inner diameter of the guide for the light source is identical to or larger than that of the guide for the incident light, The inner diameter of the guide for the incident light is identical to or smaller than the size of the measuring zone, and the inner diameter of the guide for the detector is identical to or smaller than that of the guide for the incident light. The inner diameter of the guide for the detector is 75% to 85% in size relative to that of the guide for the incident light.

In another exemplary aspect of the present disclosure, the system may further comprise a correction member and a holder which is configured to accommodating the correction member, the correction member containing an information to correct a difference or variation among the cuvettes employed for the system, and the information being processed by the processer. The difference or variation among the cuvette, which is corrected by the correction member may comprise a difference or variation in an optical path length and/or a thickness of the cuvette.

In still further exemplary aspect of the present disclosure, the system may further comprise an electronic device and a communication port, each being connected to the system, in order to exchange data with the system.

In still another exemplary aspect of the present disclosure, the system may further comprise a display showing a status, a progress of the system and/or a result of the measurement.

In still further exemplary aspect of the present disclosure, the system may further comprise a cuvette holder having a space for the cuvette, the cuvette holder being accommodated within the cuvette accommodating member. The cuvette accommodated by the cuvette accommodating member has an optical path of 0.10-0.25 mm, in particular, 0.125-0.130 mm.

In the foregoing system, the light radiating member may comprise one light source, which is configured to emit the light of both the first and the second wavelength. The light radiating member may comprise a first and a second light source in which the first light source emits the light of the first wave length and the second light source emits the light of the second wave length, or vice versa. The first wavelength is 500 nm, 530 nm, 546 nm, 570 nm or 584 nm, and the second wavelength is 800 nm or 850 nm. The first wavelength is 525-530 nm, and the second wavelength is 850 nm. The light source includes a LED, a laser diode, or a continuous light source.

Another aspect of the present provides a method for measuring the concentration of hemoglobin in whole blood using the system as disclosed herein. The method may comprise steps of: providing a cuvette containing a whole blood; installing the cuvette to the system as disclosed herein; measuring a first and a second absorbance of the whole blood in the cuvette, wherein the first absorbance is measured using a light of a first wavelength of 520 nm to 590 nm, and the second absorbance is measured using a light of a second wavelength of at least 800 nm; and processing the measured absorbance and determining the concentration of hemoglobin in the whole blood.

In the foregoing method, the first wavelength is 525-530 nm and the second wave length is 850 nm. Alternatively, the first wavelength is 500 nm, 530 nm, 546 nm, 570 nm or 584 nm, and the second wavelength is 800 nm or 850 nm.

Advantageous Effects

According to one or more embodiments of the present invention, the system of the present disclosure provides an accurate and reliable measurement of the concentration of the total hemoglobin from a relatively small amount of blood. The present system aligns the paths of the two types of incident light having different wavelengths passing through a microcuvette by using a diffuser so as to easily align a light source and thus increase the reliability of the results. In addition, the present system uses two different wavelengths so as to rapidly and accurately measure the total amount of hemoglobin, including oxidized ($HbO_2$) and reduced (Hb) form.

BRIEF DESCRIPTION OF THE DRAWINGS

The above and other objects, features and advantages of various exemplary aspects of the present invention will be more clearly understood from the following detailed description when taken in conjunction with the accompanying drawings, in which.

DETAILED DESCRIPTION OF THE EMBODIMENTS

Hereinafter, exemplary aspects of the invention will be described with reference to the accompanying drawings through which like elements are referenced by like numbers. In describing the invention, details on the structure or function of related arts are omitted if they may obscure the subject of the invention.

Figure 1:
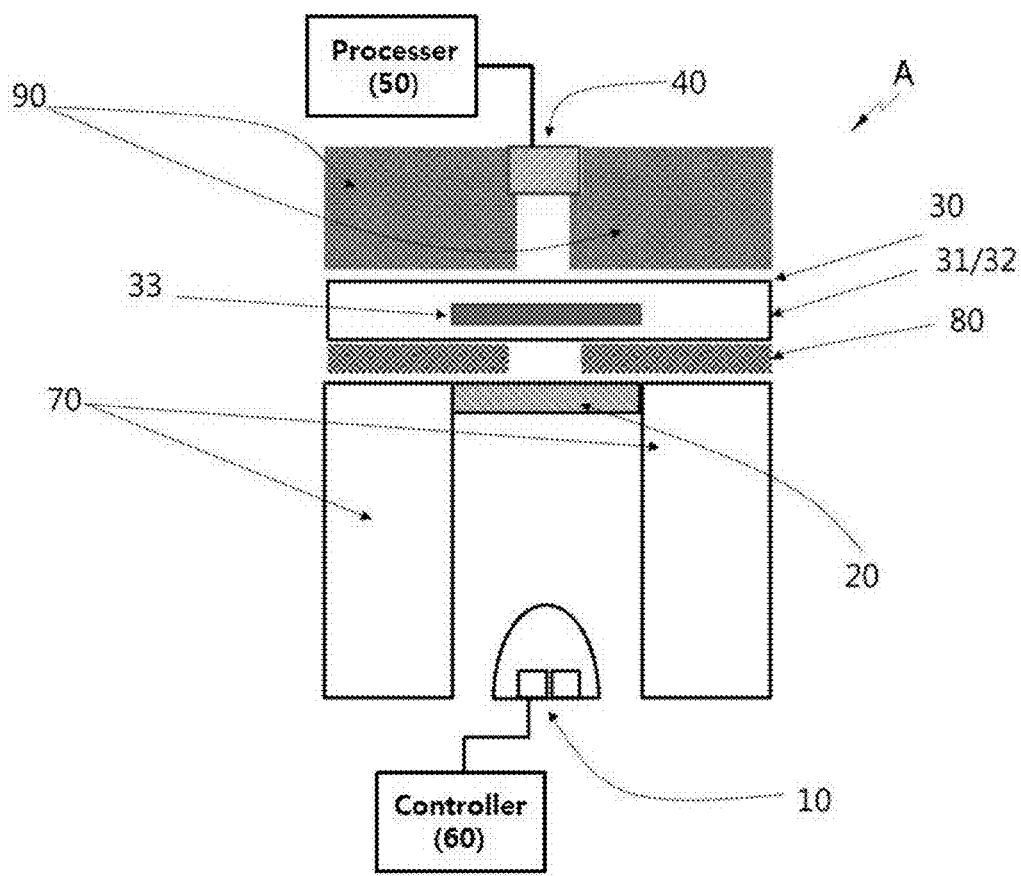
FIG. 1 is a cross-sectional view of a system according to one example of the present disclosure.
Figure 2:
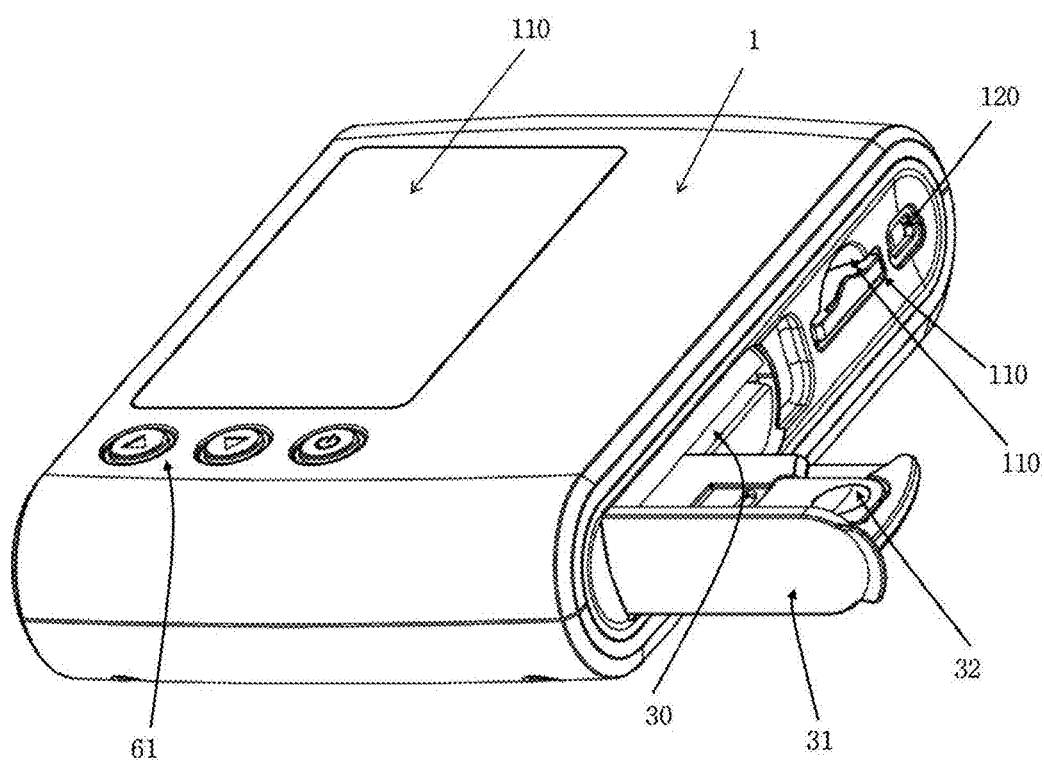
FIG. 2 is a perspective view of a system according to one example of the present disclosure.

In one aspect, the present disclosure is related to a system for measuring the concentration of hemoglobin in blood. Referring to FIGS. 1 and 2, the system of one exemplary aspect of the invention comprises a light radiating member (10) comprising at least one light source, the light source emitting an incident light having a first wavelength between 520 and 590 nm and a second wavelength of at least 800 nm; a diffuser (20) distributing the incident light emitted from the light radiating member; a cuvette accommodating member (30) configured to accommodate a cuvette for whole blood; a detector (40) detecting a first absorbance of the incident light having the first wavelength which has passed through the blood sample and a second absorbance of the incident light having the second wavelength which has passed through the blood; a processer (50) determining the amount of hemoglobin in the blood using the first and the second absorbance detected by the detector; and a controller (60) regulating the incident light such that the incident light of the first wave length and the second wave length are radiated in consecutive order.

The light source according to one embodiment of the present system emits an incident light having a first wavelength between 520 and 590 nm and/or second wavelength of at least 800 nm. The light source which may be used for the present disclosure includes a light source emitting a light with a particular wavelength, or a continuous light with a broad range of wavelength in which case a filter is used. For example, the light source may be a LED (Light emitting diode) or a laser diode without being limited thereto. In the case where the continuous light is used, a filter for filtering the light for a particular wavelength desired is used.

The light having a first wavelength and a second wavelength is emitted either from one integrated light source or from two separate light sources with each light source emitting the light with a first or a second wavelength, respectively. In one embodiment, two light sources are employed and each light source emits a first or a second wavelength of the light, respectively. While the light of a first wavelength is emitted, the light of a second wavelength is off, and the light of a first wavelength is on for a particular period of time for example, for about 1 sec to 5 sec, particularly for about 3 sec during which the light transmitted through the sample is collected and becomes off-state. Then the light of a second wavelength becomes on and the same process as described above is repeated. In the process, it is preferable that the light is incident to the sample when the light emitted is stabilized, which is controlled by a controller as described hereinafter.

When the ranges of wavelength as disclosed in the present disclosure are used, accurate results can be obtained where the value measured using capillary blood from fingertips is identical to the value measured using venous blood. For the conveniences, capillary blood from a fingertip or the heel is usually used as sample, which, however, leads to an inaccurate result because the capillary blood may not be able to represent the hemoglobin concentration in whole blood. Thus several tests are required for the accurate measurement or venous blood is required for the test instead (Yang Z W, Yang S H, Chen L, QU J, Xhu J, Tang Z. Comparison of blood counts in venous, fingertip and arterial blood and their measurement variation. Clin Lab Haem 2001; 23:155-9; Sari M, de Pee S, Martini E, et al. Estimating the revalence of anaemia: a comparison of three methods. Bull World Health Organ 2001; 79:506-11; Kayiran S M, Oezbek N, Turan M, GB. Significant differences between capillary and venous complete blood counts in the neonatal period. ClinLab Haematol 2003; 25:9-16). However, drawing blood from the vein requires a help from a specialist, and several tests causes the inconvenience to the user, which may lead to the avoidance of test by some user. Particularly, in the case in which the point of care systems is used, it is not feasible to use the venous blood for the test due to the difficulty of taking the venous blood. Thus, it is important to develop a system in which the concentration of hemoglobin is accurately measured using capillary blood.

The light source (10) according to the present disclosure emits a light of a wavelength, which has an identical or similar absorbance both to an oxidized form and a reduced form of hemoglobin. The system utilizes two different wavelengths for radiation. As for a first wavelength of light, the wavelength that has a strong absorbance both to an oxidized form and to a reduced form of hemoglobin is employed. As for a second wavelength of light, the wavelength, which has the absorbance that is lower than that of the first wavelength of light and that can be used as a background is employed. In one embodiment, the range of the first wavelength is from about 520 to 590 m, particularly about 525 nm to 550 nm, more particularly about 525 nm to 530 nm. In addition, the range of the second wavelength is at least about 800 nm, particularly about 820 nm to 900 nm, more particularly about 830 nm to 860 nm, most particularly about 850 nm. When the wavelengths that are beyond the ranges as described above are used, the absorption wavelength of an oxidized form of hemoglobin is different from that of an reduced form of hemoglobin, which results in inaccurate measurement of the hemoglobin concentration.

In other embodiment, the wavelength, which can by employed for the present system is about 500 nm, about 530 nm, about 546 nm, about 570 nm or 584 nm as the first wavelength of the light, and is about 800 nm or 850 nm as the second wavelength of the light. Alternatively, as the first wavelength of the light, at least one, for example two different wavelengths of light may also be used.

The present system includes a diffuser (20). The diffuser (20) is to distribute the light emitted from the light source evenly and to align the paths of two types of incident light having different wavelengths. The diffuser, which may be used for the present system includes ones that can convert a point light source of direct type which is compatible for the wavelengths employed for the present system to a surface light source. For example, they include a diffusing plate, or a diffusing film, or a diffusing agent without limitation. The diffuser of the present system may be made of inorganic or organic material having a light transmittance of at least about 80%, particularly about 90%, more particularly about 95%. For example, the material, which can be used for diffusing the light having at least 80% of light transmittance includes optical organic material such as cylclo olefin copolymer, Poly Methyl Meth Acrylate (PMMA), Polycarbonate (PC) and other optical inorganic materials. The people in the related art would be able to choose appropriate materials from the known ones.

The present system includes a cuvette accommodating member (30). The cuvette, which may be employed for the present system includes a microcuvette (32), an example of which includes one as described in FIG. 3. In one embodiment, the microcuvette comprises a measuring zone (33) and optical path length is about 0.10 to 0.25 mm, particularly about 0.15 mm, more particularly about 0.14 mm, most particularly about 0.13 mm, most particularly about 0.125 mm, and most particularly about 0.12 mm. Whole blood used as a sample for the hemoglobin measurement is introduced into the measuring zone, which is made of an optical material and aligned in the present system such that the light from the light source (10) can transmit through the measuring zone.

Figure 3:
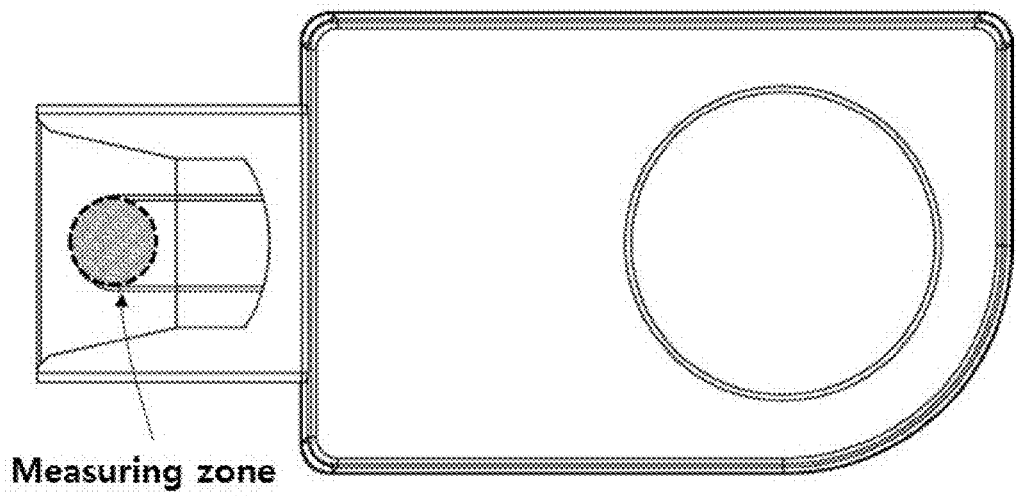
FIG. 3 is a perspective view of a microcuvette, which can be used for a system according to one example of the present disclosure.

The microcuvette employed for the present system is disposable, and ones as described in FIG. 3 may be used. For example, it comprises a body member comprising two planar plates; and a cavity formed within the body member, the cavity being defined by the two opposing inner surfaces of the plates of the body member, a portion of the cavity defining a detection zone, the body member comprising an end portion, a capillary inlet being provided at the end portion and that is communicated with the cavity, a sample slot being provided at a portion of the body member in which the capillary inlet is not formed, the sample slot being communicated with the cavity. As such, blood can be introduced to the microcuvette through the capillary inlet directly from a fingertip or can be introduced using a micropipette. The cuvette determines the amount of blood used, for example, any amount in the range of between about 1 to 50 μl of blood may be used depending on the volume of the measuring zone. The microcuvette is made of a transparent polymer by use of injection molding.

The cuvette (32) according to one embodiment of the present system is used as being installed in a cuvette holder (31), which is in turn installed into a cuvette accommodating member (30) as shown in FIG. 2. The cuvette holder (31) is used to guide the measuring zone of the microcuvette to a right position relative to the light source for accurate measurement. Further, by using the cuvette holder (31), cuvette's in and out of the system becomes convenient. By using the holder, the cuvette is shielded from the light other than from the light source (10), which leads to an accurate measurement. By using the holder, the cuvette is installed into the system at an optimum speed which makes the cuvette being inserted or installed into the system under the force that is identical to or smaller than that of capillary force exerted on the blood sample and thus the tilting of the blood in the measuring zone to one side is prevented due to an abrupt action during the installation. To this end, the present system includes a cuvette holder (31) for a cuvette, which is accommodated into the cuvette accommodating member (30).

The present system includes a detector (40). The detector detects the absorbance of the light of the first wavelength that has passed the blood sample and the absorbance of the light of the second wavelength. The light of each wavelength emitted from the light source (10) is transmitted through the blood sample and the transmitted light is then detected by the detector. The first and second absorbance of the light of the first and the second wavelength are measured by the detector after their transmission through the blood sample. At least one reading of the absorbance is performed, which is in turn processed by the processer as described hereinafter.

The present system comprises a processer (50). The processer processes the first and second absorbance readings so as to calculate or determine the concentration of hemoglobin in whole blood from the readings using a certain algorithm. In one embodiment, the algorithm employed may be integrated into the present system as a program and the calculated value can be displayed on a display (100) of the present system as described hereinafter.

In one embodiment, the algorithm of the processer (50) of the present system calculates the concentration of hemoglobin using the following formula:

$$[\text{concentration of total hemoglobin}] = (\text{Abs}_1 - \text{Abs}_2) \cdot K_1 + K_2.$$

In the formula, $\text{Abs}_1$ is the absorbance of the light of the first wavelength, and $\text{Abs}_2$ is the absorbance of the light of the second wavelength. $K_1$ and $K_2$ are a coefficient the value of which relies on the measuring device used, wavelength and/or optical path of cuvette employed and the like. For example, $K_1$ is a constant that determines the discrimination capacity according to the hemoglobin concentration, and $K_2$ is a correction constant.

These coefficients are used to correct the fine differences in the dimension of the cuvette employed. The cuvettes have some variation from batch to batch, for example; the differences exist in the optical path length of the measuring zone or the thickness of the planar plates of the cuvette. Therefor, the dimension of a cuvette from a particular batch is put into the system by use of a chip, from which the coefficient can be calculated. The coefficient is also used to correct the differences or variations in the measurement due to the cuvette variation.

In this perspective, the present system further comprises a correction member (111) and a holder (110) which is configured to accommodate the correction member. The correction member contains information to correct a difference or variations among the cuvettes as described above. The correction member may be a chip that contains information regarding a particular batch of cuvette. For example, the dimension of a cuvette from a particular batch is coded and the code is recorded on a chip. The chip is inserted into the holder (110), and the information within the chip is used to calculate the concentration of hemoglobin.

The present system comprises a controller (60). The controller controls the light from the light source such that the lights of a first wavelength and a second wavelength are radiated in a sequential order. The light of the first wavelength is radiated followed by the light of the second wavelength or vice versa and in-between, the controller controls the light of each wavelength so that the amount of each light radiated is stabilized.

The present system further comprises at least one guide, which makes the light of the first and the second wavelength being accurately incident upon the measuring zone of the cuvette, and which also makes only the transmitted light that has passed through the sample being detected by the detector. Thus by using the guides, accurate measurement with reduced noise can be obtained.

In this perspective, the present system further comprises a guide for the light source (70) directing or guiding the incident light to the diffuser; a guide for the incident light (80) directing or guiding the light incident upon the diffusion member to a measuring zone of the cuvette containing whole blood; and a guide for the detector (90) directing or guiding the light that has passed through the measuring zone to the detector.

By using the guide, accurate measurement can be obtained. The guide for the light of the first and the second wavelength from the light source (70) makes the light to be radiated to the diffuser following the same optical path. The light, which has passed through the diffuser is then guided to and passes though the measuring zone of the cuvette by the guide for the incident light (80). The transmitted light is guided to the detector and detected by the guide for the detector (90). To this ends, the inner diameter of the guide for the light source is configured to be identical to or larger than that of the guide for the incident light, and the inner diameter of the guide for the incident light is configured to be identical to or smaller than the size of the measuring zone and the inner diameter of the guide for the detector is configured to be identical to or smaller than that of the guide for the incident light. In one embodiment, the inner diameter of the guide for the detector is about 95% to 70%, particularly about 90% to 75%, more particularly about 85% to 75% in size relative to that of the guide for the incident light.

For accurate measurement, it is preferable that the diffuser, the cuvette accommodating member, and the detector are arranged for example as exemplified in FIG. 1 and positioned in close proximity. For example, the dimension of the system is about 100 mm×150 mm (width and length) and they are positioned within for example about 10 mm in distance from each other, particularly about 7 to 9 mm, more particularly about 6 mm. The distance from the light source to the diffuser is various depending on the factors such as the quality of the diffuser determines the efficiency of the conversion of a point light to a surface light, the intensity of the light source, the optical path length of the cuvette, and the dimension of the system employed and is for example about not more than 5 mm, and particularly not more than 3 mm.

The present system further comprises a display (100). The display shows the status, progress of the system and/or results of the measurement such as the absorbance and the concentration of hemoglobin.

The present system further comprises an electronic device and a communication port (120), each being connected to the system. They are used for exchanging data with the present system. The electronic device refers to a device for storage of the hemoglobin data measured and for data analysis to provide information to diagnose a disease. For example, it may include a computer, a printer, a cell phone, and/or a smart phone, but is not limited thereto.

According to one embodiment, the components that are comprised in the present system can be positioned or arranged in a housing (1) as shown in FIG. 2. In other embodiment, the processor (50) or the controller (60) of the present system may be present as integrated in the present system with the other components or may be present separately from the other components. The processer and the controller may be configured as a unit as well.

In other aspect, the present invention relates to a method for determining the concentration of hemoglobin from whole blood using the present system as described above. The present method is used for the determination of total hemoglobin, that is, the oxidized and the reduced form of hemoglobin, contained in the blood.

The present method, for example, can be performed using the following steps.

That is, the present method comprises steps of providing a cuvette containing a whole blood; installing the cuvette to the system of the present disclosure; measuring a first and a second absorbance of the whole blood in the cuvette, wherein the first absorbance is measured using a light of a first wave length of 520 nm to 590 nm, and the second absorbance is measured using a light of a second wave length of at least 800 nm; and processing the measured absorbance and determining the concentration of hemoglobin in the whole blood.

The types of the light source, which may be used and the ranges of the wavelength are as described above. In one embodiment, the first wavelength is about 525-530 nm and the second wave length is 850 nm. In other embodiment, the first wavelength is about 500 nm, about 530 nm, about 546 nm, about 570 nm and/or about 584 nm, and the second wavelength is about 800 nm or 850 nm.

The determination of the concentration of hemoglobin is performed using an algorithm as described above. Also, the system used for the present method is as described above.

The present method is used to determine the concentration of the hemoglobin in whole blood. Hemoglobin is an iron containing protein present in red blood cells and is the primary vehicle for transporting oxygen in the blood. Under certain conditions, oxygen bound to the hemoglobin is released into the blood's plasma and absorbed into the tissues. Four oxygen molecules are bound to one molecule of hemoglobin and the degree of saturation is determined by how much of that capacity is filled by oxygen at any time. The oxygen-carrying capacity of hemoglobin is determined by the type of hemoglobin present in the blood. The amount of oxygen bound to the hemoglobin at any time is related, in large part, to the partial pressure of oxygen to which the hemoglobin is exposed. Generally, partial pressure of oxygen is typically higher in arterial bloods than in venous bloods. The hemoglobin content is expressed as an average of the hemoglobin concentration contained in a certain volume of red blood cells. Red blood cell indices are blood tests that provide information about the hemoglobin content and size of red blood cells and include average red blood cell size, hemoglobin amount per red blood cell and the amount of hemoglobin relative to the size of the cell per red blood cell. Abnormal values indicate the presence of anemia and the indices are different depending on the types of anemia. Thus, the accurate measurement is important. The hemoglobin content can also be used as an index for iron deficiency. Thus, the content can be used for monitoring the efficacy of an iron therapy or diagnosis of the disease due to the iron deficiency.

While a few exemplary embodiments of the present invention have been shown and described, it would be appreciated by those skilled in the art that changes may be made to these exemplary embodiments without departing the principles and spirit of the invention, the scope of which is defined by the claims and their equivalents.

DESCRIPTION OF THE NUMERALS USED

| | |
|---|---|
| 10: light radiating member | 20: diffuser |
| 30: cuvette accommodating member | 31: cuvette holder |
| 32: cuvette | 33: measuring zone of the cuvette |
| 40: detector | 50: processer |
| 60: controller | 61: button for the controller |
| 70: guide for the right source | 80: guide for incident light |
| 90: guide for detector | 100: display |
| 110: holder for correction member | 111: correction member |
| 120: communication port | |

What is claimed is:

1. A system for measuring the concentration of hemoglobin in whole blood, the system comprising:

a light radiating member comprising at least one light source, the light source emitting an incident light having a first wavelength of 546 nm, 570 nm or 584 nm and a second wavelength of 800 nm or 850 nm;

a diffuser distributing the incident light emitted from the light radiating member;

a guide for the light source guiding the incident light to the diffuser;

a cuvette accommodating member configured to accommodate a cuvette for whole blood;

a guide for the incident light guiding the light incident upon the diffuser to a measuring zone of the cuvette comprising the whole blood;

a detector detecting a first absorbance of the incident light having the first wavelength which has passed through the whole blood and a second absorbance of the incident light having the second wavelength which has passed through the whole blood;

a guide for the detector guiding the incident light that has passed through the measuring zone to the detector;

a processer determining the amount of hemoglobin in the whole blood using the first and the second absorbance detected by the detector; and a controller regulating the incident light such that the incident light of the first wave length and the second wave length are radiated in a sequential order, wherein:

the guide for the light source has an inner diameter which is identical to or larger than that of the guide for the incident light;

the guide for the incident light has an inner diameter which is identical to or smaller than the size of the measuring zone; and the guide for the detector has an inner diameter which is identical to or smaller than that of the guide for the incident light.

2. The system of claim 1, which further comprises an electronic device and a communication port for exchanging data.

3. The system of claim 1, which further comprises a display showing a status, a progress of the system and/or a result of a measurement.

4. The system of claim 1, which further comprises a cuvette holder having a space for the cuvette, the cuvette holder being accommodated within the cuvette accommodating member.

5. The system of claim 1, wherein the light radiating member comprises one light source which is configured to emit light of both the first and the second wavelength.

6. The system of claim 1, wherein the light source is a LED, a laser diode, or a continuous light source.

7. The system of claim 1, wherein the light source includes a first light source emitting a first incident light having the first wavelength and a second light source emitting a second incident light having the second wavelength, and wherein the diffuser distributes evenly and aligns paths of the first and second incident lights emitted from the first and second light sources.

8. The system of claim 1, wherein the inner diameter of the guide for the detector is 75% to 85% in size relative to that of the guide for the incident light.

9. The system of claim 1, which further comprises a holder which is configured to accommodating a correction member, the correction member containing an information to correct a difference among the cuvettes used for the system, and the information being processed by the processer.

10. The system of claim 1, wherein the light radiating member comprises a first and a second light source in which the first light source emits the light of the first wavelength and the second light source emits light of the second wavelength, or vice versa.

11. The system of claim 1, wherein the first wavelength is 546 nm, and the second wavelength is 850 nm.

12. The system of claim 1, wherein the cuvette accommodated by the cuvette accommodating member has an optical path of 0.10-0.25 mm.

13. A method for measuring the concentration of hemoglobin in whole blood using the system according to claim 1, which comprises the steps of:
 providing the cuvette containing the whole blood;
 installing the cuvette containing the whole blood;
 measuring the first and the second absorbance of the whole blood in the cuvette, wherein the first absorbance is measured using light of the first wavelength of 546 nm, 570 nm or 584 nm, and the second absorbance is measured using light of the second wavelength of 800 nm or 850 nm; and
 processing the measured absorbances and determining the concentration of hemoglobin in the whole blood.

14. A method for measuring the concentration of hemoglobin in whole blood using the system according to claim 8, which comprises the steps of:
 providing the cuvette containing the whole blood;
 installing the cuvette containing the whole blood;
 measuring the first and the second absorbance of the whole blood in the cuvette, wherein the first absorbance is measured using light of the first wavelength of 546 nm, 570 nm, or 584 nm, and the second absorbance is measured using light of the second wavelength of 800 nm or 850 nm; and
 processing the measured absorbances and determining the concentration of hemoglobin in the whole blood.

15. The system of claim 9, wherein the difference among the cuvettes which is corrected by the correction member comprises an optical path and/or a thickness of a cuvette.

16. A method for measuring the concentration of hemoglobin in whole blood using the system according to claim 10, which comprises the steps of:
 providing the cuvette containing the whole blood;
 installing the cuvette containing the whole blood;
 measuring the first and the second absorbance of the whole blood in the cuvette, wherein the first absorbance is measured using light of the first wavelength of 546 nm, 570 nm, or 584 nm, and the second absorbance is measured using light of the second wavelength of 800 nm or 850 nm; and
 processing the measured absorbances and determining the concentration of hemoglobin in the whole blood.

17. A method for measuring the concentration of hemoglobin in whole blood using the system according to claim 11, which comprises the steps of:
 providing the cuvette containing the whole blood;
 installing the cuvette containing the whole blood;
 measuring the first and the second absorbance of the whole blood in the cuvette, wherein the first absorbance is measured using light of the first wavelength of 546 nm, and the second absorbance is measured using light of the second wavelength of 850 nm; and
 processing the measured absorbances and determining the concentration of hemoglobin in the whole blood.

18. The system of claim 12, wherein the cuvette accommodated by the cuvette accommodating member has an optical path of 0.125-0.130 mm.

19. The method of claim 13, wherein the first wavelength is 546 nm and the second wavelength is 850 nm.

* * * * *